United States Patent [19]
Greenfield

[11] Patent Number: 5,984,931
[45] Date of Patent: Nov. 16, 1999

[54] DIAGNOSTIC MEASUREMENT TRANSFER APPARATUS

[76] Inventor: Bruce G. Greenfield, 9 Fieldstone La., Bryn Mawr, Pa. 19010

[21] Appl. No.: 08/820,197

[22] Filed: Mar. 18, 1997

[51] Int. Cl.$^6$ .................................................... A61B 5/00
[52] U.S. Cl. ........................... 606/130; 600/425; 33/515
[58] Field of Search .................................. 600/411, 417, 600/414, 425–427; 128/845; 606/130; 33/511, 512, 515; 378/162–164

[56] References Cited

U.S. PATENT DOCUMENTS

| | | |
|---|---|---|
| 2,226,708 | 12/1940 | Cleary . |
| 3,073,310 | 1/1963 | Mocarski . |
| 3,508,552 | 4/1970 | Hainault . |
| 4,341,220 | 7/1982 | Perry . |
| 4,427,005 | 1/1984 | Tener . |
| 4,580,561 | 4/1986 | Williamson . |
| 4,617,925 | 10/1986 | Laitinen . |
| 4,618,978 | 10/1986 | Cosman .................................. 378/164 |
| 4,706,665 | 11/1987 | Gouda . |
| 4,841,975 | 6/1989 | Woolson . |
| 4,918,715 | 4/1990 | Krupnick et al. ........................ 378/164 |
| 5,031,203 | 7/1991 | Trecha ..................................... 350/600 |
| 5,193,106 | 3/1993 | DeSena .................................... 378/163 |
| 5,260,985 | 11/1993 | Mosby .................................... 378/164 |
| 5,437,280 | 8/1995 | Hussman ................................. 600/417 |

*Primary Examiner*—Ruth S. Smith
*Attorney, Agent, or Firm*—Seidel, Gonda, Lavorgna & Monaco, PC

[57] ABSTRACT

An apparatus and method is provided for transferring measurements from a diagnostic image to a body site. The apparatus includes a fixture having channels formed along its length. A removable template is provided which can be removably positioned in the fixture. The template is marked corresponding to a diagnostic image on an X-ray film. A positioning block is provided which is adapted to slide along the length of the channels formed in the fixture. The positioning block includes a positionable indicator having an indicator head. The indicator head has a guide aperture therethrough. The indicator head is positioned over the mark on the template corresponding to the diagnostic image. A patient's body part, for example a foot, is then aligned with the fixture. The template is removed from the fixture, and a mark is made on the patient's body using the guide aperture, thereby allowing a physician to directly mark a site on the patient's body.

49 Claims, 4 Drawing Sheets

DIAGNOSTIC MEASUREMENT TRANSFER APPARATUS

FIELD OF THE INVENTION

The present invention relates to a device and method for use in accurately and easily transferring the location of a measurement from a diagnostic image, such as, for example, a podiatric X-ray to a body site, such as a foot. The present invention provides a more convenient and accurate means for accomplishing this task than prior methods. Although described in the context of podiatry and podiatric surgery, the invention is not so limited, and is applicable to all forms of medical and surgical procedures.

BACKGROUND OF THE INVENTION

A common problem encountered in the field of podiatric medicine is determining the proper location at which to incise a patient's foot in order to perform a surgical procedure. Surgical treatment of podiatric medical problems generally involves a podiatrist or other physician creating an incision corresponding to the location of the problematic area. It is crucial that the point of incision be accurately located on the patient's body. Otherwise, the patient runs the risk of multiple incisions, and an increase in the time of surgery. An incision made at the wrong cite can also risks new injuries and possible further complications.

One example of where a proper point of incision is critical is in the treatment of bone spurs. Bone spurs are outgrowths of bone caused by the buildup of calcium deposits due to excessive stress at points where ligaments and/or tendons attach to bone. Bone spurs often appear on X-ray film as small protrusions extending from the heel of the foot.

Accurately locating a proper incision point on the patient's foot corresponding to a podiatric growth viewed on an X-ray film poses several problems to the physician. While many podiatric growths, such as bone spurs, are discernible by X-ray, the physician must visually estimate the corresponding location of the point of incision on the patient's foot. It is impractical, if not impossible, to attempt to locate an incision point on a patient's foot from a corresponding X-ray film, in part because X-ray images are only two-dimensional.

Further, it is impossible for the physician to both incise the proper area and simultaneously view the X-ray film. Currently, a physician must attempt to use a ruler to transfer the X-ray measurement to a patient's foot. The physician first measures the location to be incised on the X-ray along the X and Y axes. These measurements are then transferred to the patient's foot using the ruler. However, because the X-ray produces a two-dimensional representation, the X and Y measurements taken from the X-ray film with a ruler do not take into account the curvature of the foot. Therefore, this method does not bridge the gap from two to three dimensions, and often produces inaccurate results.

Otherwise, the physician must either look back and forth from the film to the patient, or have another member of the surgical team hold the X-ray film near the patient's body. Either of these options affords the physician only an approximation of the proper incision point.

There is, accordingly, a need for a device for accurately and easily transferring the location of an anatomical feature from a diagnostic image to a body site.

There is also the need for a diagnostic device which accurately transfers a measurement taken from a two-dimensional image to a three-dimensional body part.

SUMMARY OF THE INVENTION

The present invention is directed to a device that satisfies the need for the accurate and easy transfer of measurements from a diagnostic image directly to the corresponding site on a patient's body. The present invention provides a truly innovative and effective solution to this need at a cost to the user that is insignificant compared to the accuracy, convenience and surgical benefits it produces.

A device having features of the present invention comprises a fixture for receiving a body part onto which a measurement is to be transferred. A template is provided which is removably attachable to the fixture. The template is placed over the diagnostic image, and the measurement is transferred to the template. The template is then attached to the fixture.

An indicator is provided which is movable in orthogonal directions relative to the fixture and the template. The indicator is aligned with measurement which has been transferred to the template. A body part is then received into the fixture, and the body part is incised at the proper site using the indicator as a guide.

The present invention provides the physician with an accurate and practical means of marking an incision site directly onto a patient's body.

The present invention also decreases the time needed for a surgical procedure by allowing a physician to quickly locate an incision site.

DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

Figure 1:
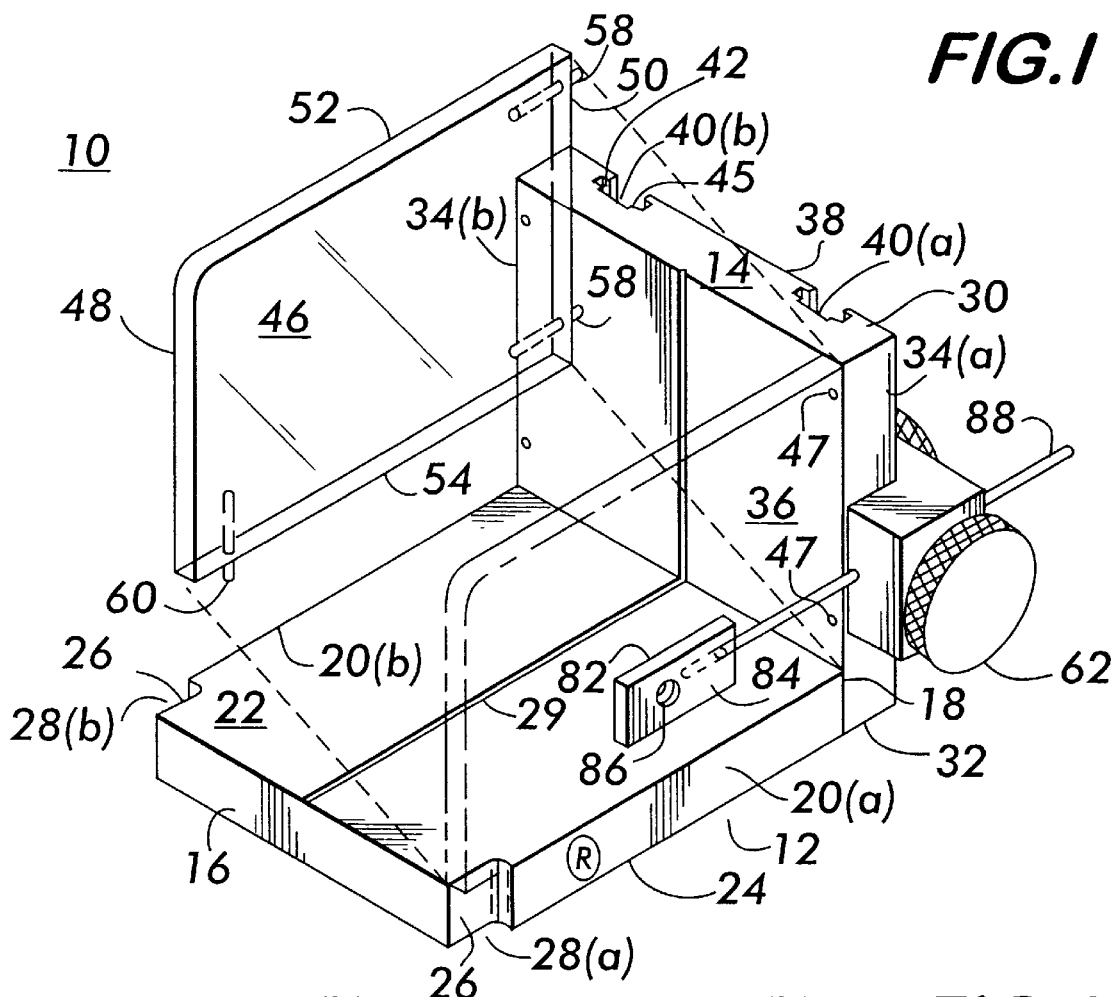
FIG. 1 shows a perspective view of the present invention.

Referring to the drawings, wherein like numerals refer to like elements, the present invention generally comprises an apparatus for transferring the position of an anatomical feature from a diagnostic image, such as, for example, an X-ray directly to the corresponding site on a patient's body. As shown in FIG. 1, the apparatus comprises a fixture 10, formed from polycarbonate or other suitable material. In the preferred embodiment, the fixture 10 has a base 12 and an upstanding wall 14 disposed at right angles to the base 12.

The base 12 has a first edge 16, a second edge 18, side edges 20(*a*) and 20(*b*), a first surface 22, and a second surface 24. In the preferred embodiment, the base 12 has indentations 26 located at opposite corners 28(*a*) and (*b*) where the side edges 20(*a*) and 20(*b*) meet the first edge 16.

In the preferred embodiment, a centering guide 29 is scribed or otherwise formed in or on the fixture 10. Additionally, the base may be provided with markings indicating the proper orientation for the right or left side of the body part to be received onto the fixture 10, which markings help to position the foot in the proper orientation with relation to the image taken in the X-ray film. In the drawings, this is shown by the circled R scribed or otherwise formed on the base 12, indicating the right side.

Figure 2:
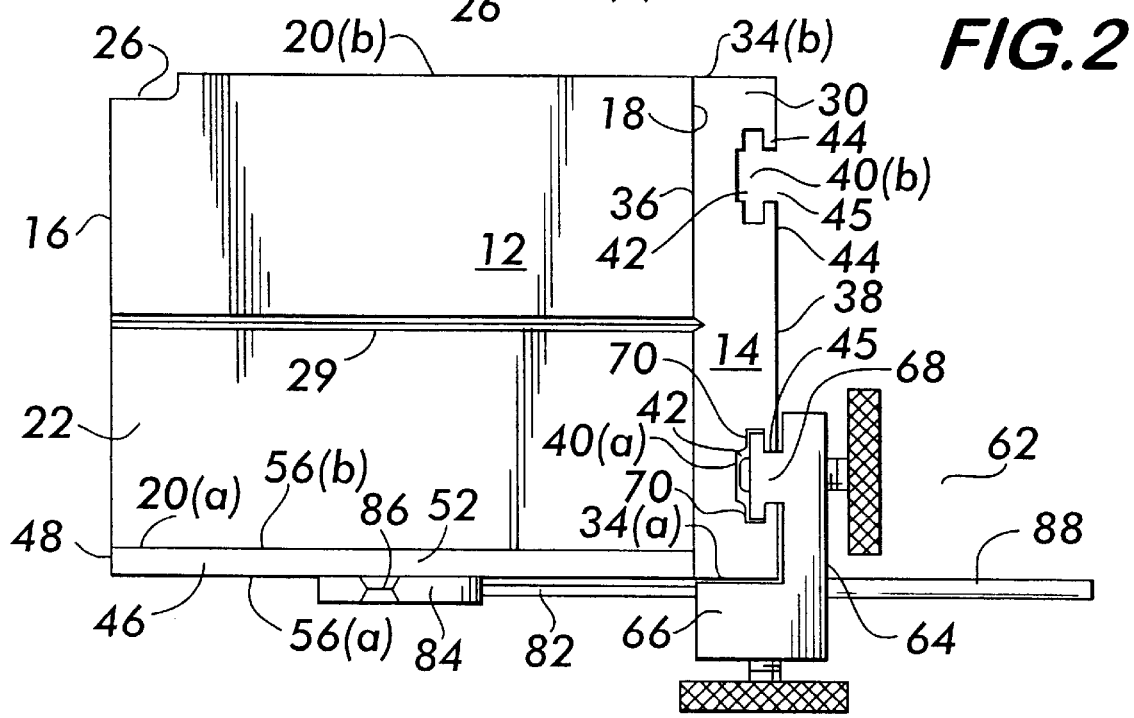
FIG. 2 shows a first plan view of the present invention.
Figure 4:
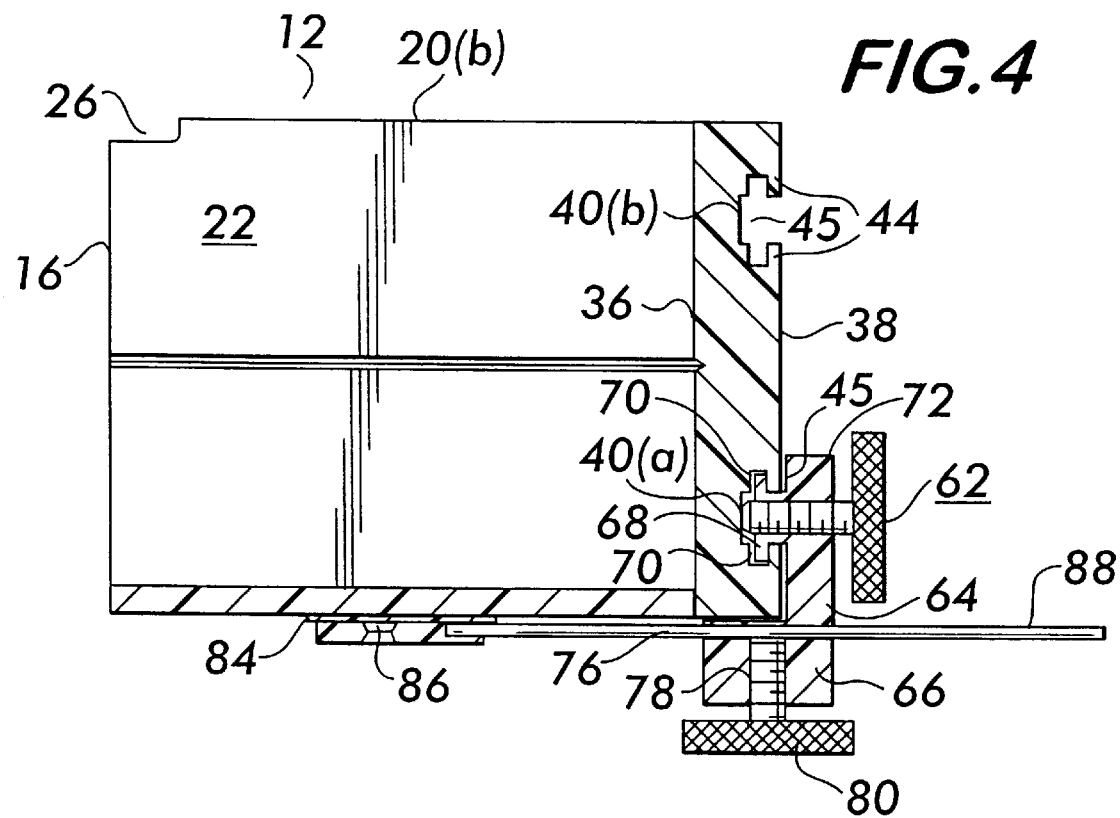
FIG. 4 shows a cross sectional view taken along line 4—4 in FIG. 3.

As shown in FIGS. 1 and 2, the upstanding wall 14 has a first edge 30, a second edge 32, a base edges 34(a) and 34(b), a first face 36, and a second face 38. Channels 40(a) and 40(b) are formed along the length of the upstanding wall 14, and have openings 42, 45 in the first edge 30, the second edge 32, and the second face 38. As shown in FIGS. 2 and 4, opposing flanges 44 constrict the channel openings 45 in the second face 38 of the upstanding wall 14. The first face 36 of the upstanding wall 14 has a plurality of openings 47 disposed adjacent the side edges 34(a) and 34(b). It is also appreciated that rather than a plurality of openings, a channel may be formed in the face of the upstanding wall adjacent the side edges.

The first face 36 of the upstanding wall 14 is attached to the second edge 18 of the base 12 adjacent the second edge 32 of the first face 36. However, it is also contemplated that the fixture 10 may be molded from a single piece of polycarbonate or other material without departing from the invention. It is also contemplated that the fixture may be formed without a base. In the preferred embodiment, a centering guide 29 is further scribed or otherwise formed in or on the upstanding wall 14.

Figure 3:
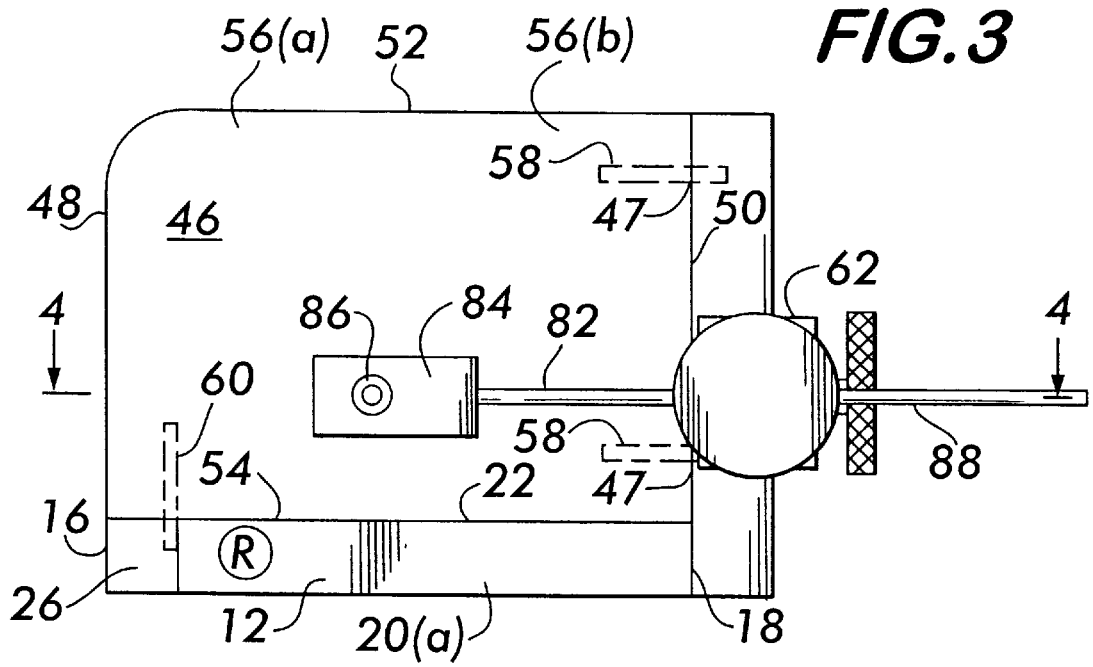
FIG. 3 shows a side view of the present invention.

As shown in FIGS. 2 and 3, a removable template 46 is provided, formed preferably from transparent polycarbonate or other suitable material. The template 46 has a first edge 48, a second edge 50, a top edge 52, a bottom edge 54, and opposite marking surfaces 56(a) and 56(b). A plurality of locator pins 58 are disposed along the second edge 50 of the template 46 in alignment with the openings 47 of the first face 36 of the upstanding wall 14. The locator pins 58 are adapted to removably engage the openings 47. In the preferred embodiment, a locator pin 60 is also disposed along the bottom edge 54 of the template 46 adjacent the first edge 48 of the template 46. The locator pin 60 is adapted to rest against the indentations 26 found in the base 12. In this manner, the indentations 26 act to help align the template 46.

As shown in FIGS. 2 and 4, a positioning block 62 slideably engages a selected one of the channels 40(a) and 40(b) of the upstanding wall 14. In the preferred embodiment, the positioning block 62 has a first wall 64 and a second wall 66. The first wall 64 has a shoe 68 extending therefrom. The shoe 68 is adapted to slideably engage a selected one of the channels 40(a) and 40(b). The shoe 68 has flanges 70 which extend outwardly therefrom, and flare into the selected channel 40(a) and 40(b). In the preferred embodiment, a first threaded aperture 72 is provided in the first wall 64 for engaging a first set screw 74.

The second wall 66 has a bore 76 extending therethrough. A side threaded aperture 78 is disposed in the side wall which engages a second set screw 80. The side threaded aperture 78 intersects the bore 76.

An indicator 82 is also provided. In the preferred embodiment, the indicator 82 has an indicator head 84 having a guide aperture 86 therethrough. A positioning rod 88 extends from the indicator head 84, and slideably engages the bore 76. By use of the positioning block, the indicator is adjustable along the X- and Y-axes in relation to the template 46.

Figure 6:
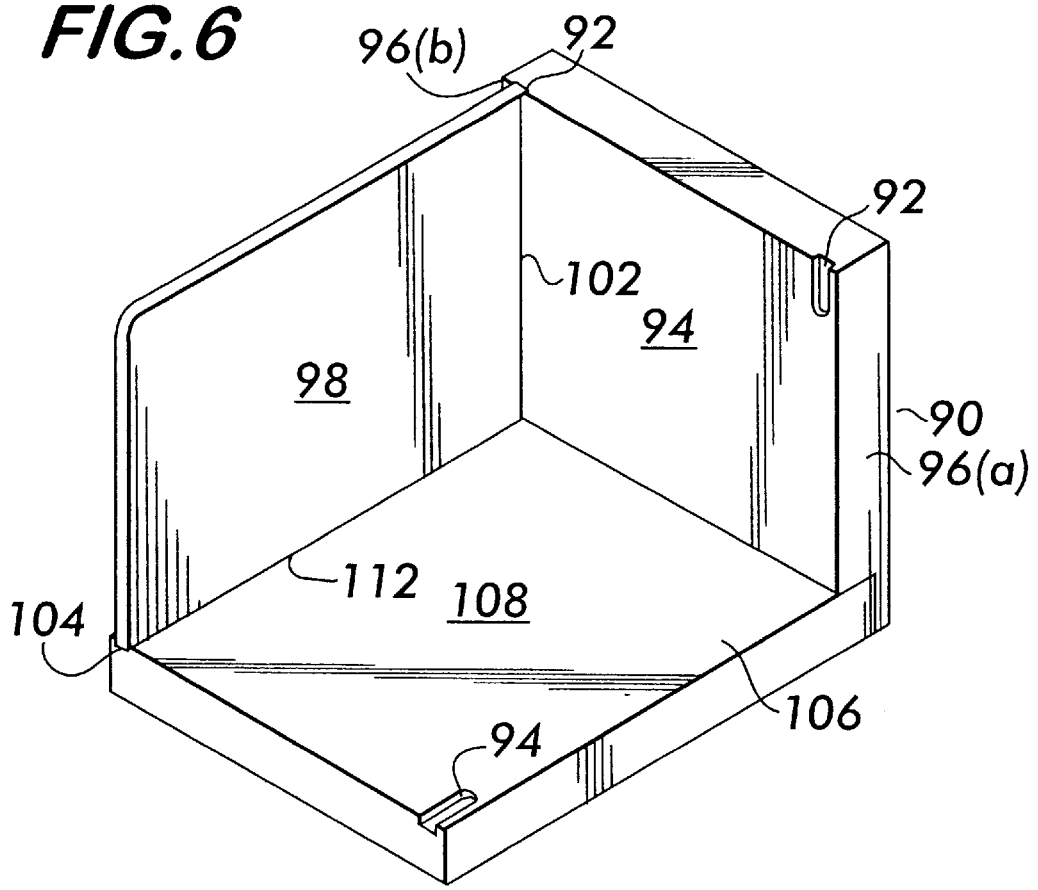
FIG. 6 shows a perspective view of a second embodiment of the present invention.
Figure 7:
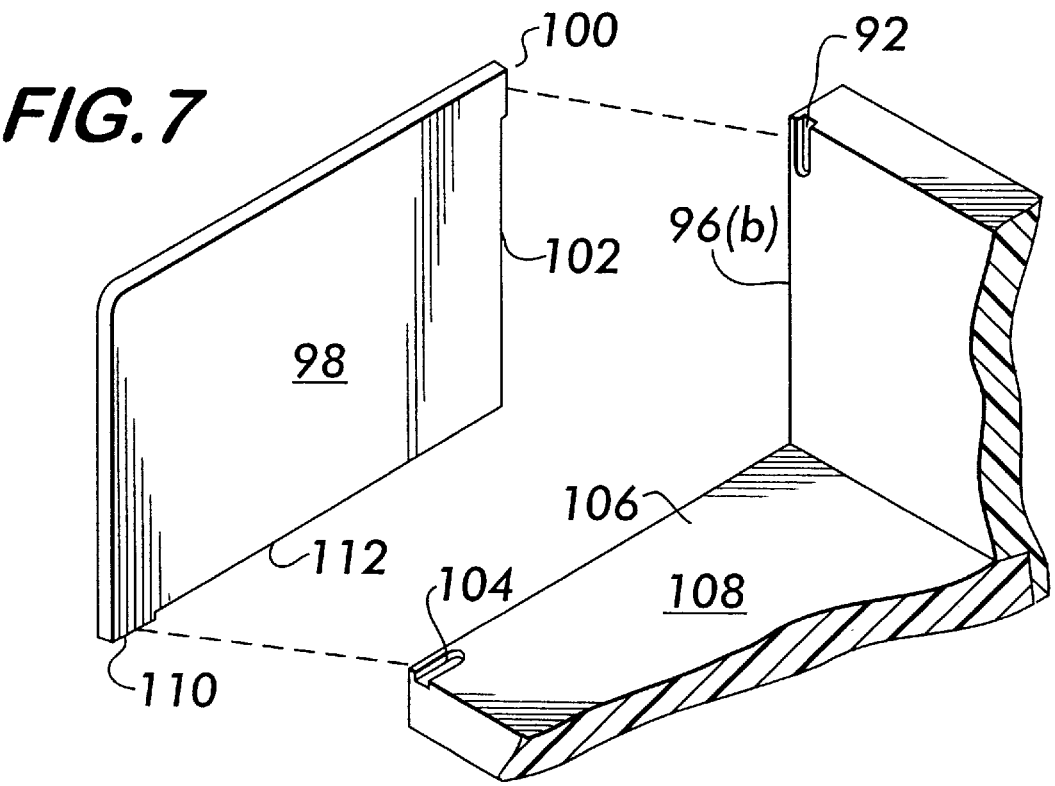
FIG. 7 shows an exploded partial perspective view of the second embodiment of the present invention shown in FIG. 6.

In a second embodiment of the present invention, the template is detachably positioned on the fixture using suitably-formed projections rather than pins. In this embodiment, as illustrated in FIGS. 6 and 7, the upstanding wall 90 can be formed with grooves 92 in its first face 94, disposed adjacent the side edges 96(a) and 96(b) of the upstanding wall 90. The template 98 has integrally formed projections 100 along its second edge 102 in alignment with the grooves 92. The projections 100 are adapted to removably engage the grooves 92. A groove 92 can also be formed on the first face 106 of the base 108, with a corresponding projection 110 formed on the bottom edge 112 of the template 98.

The present invention may be used by a physician as follows. The template 46 is detached from the fixture 10, and is placed over, for example, an X-ray image (not pictured) displaying an image of the foot to be incised. The template 46 is manipulated so that the second edge 50 of the template 46 is aligned with the heel of the foot as shown in the X-ray image, and the second edge 54 of the template is aligned with the sole of the foot as shown in the X-ray image. A locator mark M such as an X is made upon either marking surface 56(a) or 56(b) of the template 46 using a suitable marker. The mark is depicted in FIGS. 1 and 3 as an "X."

The template 46 is then inserted into the fixture 10 adjacent the area of the foot (left side or right side) where the incision will be made. As shown in FIG. 3, the second locator pins 58 of the template fit snugly into the openings 47 on the first face 36 of the upstanding wall 14. The lower pin 60 rests against the indentation 26 formed in the corner 28 of the base 12, and aids in properly aligning the template 46.

The positioning block 62 is then inserted into the selected channel 40(a) or 40(b) adjacent the side of the fixture 10 where the template 46 has been inserted. The positioning rod 88 of the indicator 82 is inserted into the bore 86 of the positioning block 62.

The indicator 82 is then adjusted so that the guide aperture 86 of the indicator head 84 is centered over the center of the locator mark M on the template 46. Adjustment of the indicator 82 is accomplished as follows.

The indicator 82 is adjusted along the Y-axis by moving the positioning block 62 along the length of the channel 40. When the positioning block 62 holds the indicator 82 at the desired vertical height, the first set screw 72 is turned. Tightening the first set screw 72 causes the flanges 70 of the shoe 68 to be forced against the opposing flanges 44 of the second face 38 of the upstanding wall 14. This holds the positioning block 62 firmly in the channel 40(a) or 40(b) at the desired vertical height.

To align the indicator 82 along the X-axis, the second set screw 88 is first in the loosened position. In this position, the indicator positioning rod 88 is free to slide along the bore 86. Once the guide aperture 86 is directly over the center of the locator mark M on the marking surface 56 of the template 46, the second set screw 88 is turned. This forces the second set screw against the indicator positioning rod 88 and holds the rod 88 firmly in place.

Figure 5:
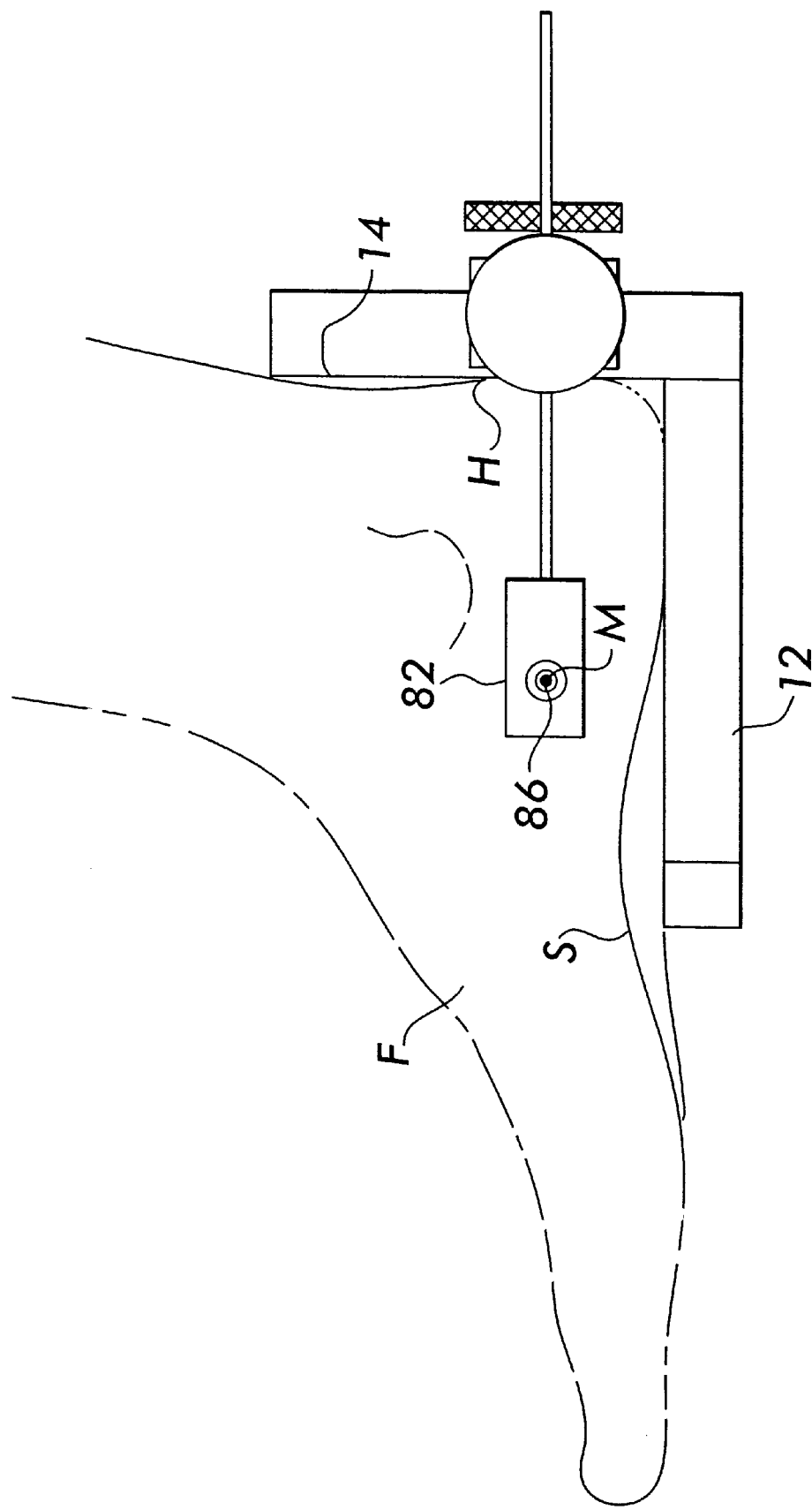
FIG. 5 shows the fixture in use in marking a diagnostic site on a patient's body.

The template 46 is then removed from the fixture 10. As shown in FIG. 5, a patient's foot F is aligned with the fixture with the sole S of the foot touching the base 12, while the heel H of the foot is placed against the upstanding wall 14. The position of the indicator 82 now matches the alignment of the template 46 with the diagnostic image. A marking device, by way of illustration, a felt tip or other suitable marker, is then inserted through the guide aperture 86, and a mark M is made on the patient's foot F corresponding to the proper incision point. The physician may then make the appropriate incision.

It is also contemplated that a means other than a marker can be used to pinpoint the proper incision point on a patient's foot. For example, a laser, diode, or other light beam may be shown through the guide aperture. The light beam will shine on the patient's foot at the exact point of incision.

It is further appreciated that the present invention is applicable to surgical procedures other than those involving the foot. For example, the present invention may be easily adapted to transfer measurements from a diagnostic image to a patient's elbow or cranium.

The present invention may be embodied in other specific forms without departing from the spirit or essential attributes thereof and, accordingly, reference should be made to the appended claims, rather than to the foregoing specification, as indicating the scope of the invention.

What is claimed is:

1. An apparatus for use in transferring measurements from a diagnostic image to a body site, comprising:
   (a) a fixture for receiving a body part onto which a measurement is to be transferred;
   (b) a template removably attached to the fixture onto which a measurement may be transferred from a diagnostic image;
   (c) an indicator movable relative to the fixture and the template, the indicator being movable in orthogonal directions; and,
   (d) a positioning block, wherein the indicator is in sliding engagement with the positioning block, the positioning block for permitting movement of the indicator in orthogonal directions relative to the fixture and the template, wherein the positioning block slideably engages the fixture.

2. An apparatus for use in transferring measurements from a diagnostic image to a body site, comprising:
   (a) a fixture for receiving a body part onto which a measurement is to be transferred, the fixture having a first edge, a second edge, side edges, a first face, and a second face;
   (b) a template removably attached to the fixture, the template having a first edge, a second edge, and opposite marking surfaces;
   (c) a positioning block slideably mounted on the fixture;
   (d) an indicator in sliding engagement with the positioning block, whereby the indicator is moveable in orthogonal directions relative to the fixture and template.

3. The apparatus according to claim 2, wherein the fixture has a channel formed along its length adjacent one of the side edges, the channel open to the first edge or the second edge of the fixture, the channel open to the second face of the fixture.

4. The apparatus according to claim 3, wherein the second face of the fixture has flanges constricting the channel opening in the second face of the fixture.

5. The apparatus according to claim 3, wherein the positioning block has a bore therethrough.

6. The apparatus according to claim 5, wherein the indicator is in slidable engagement with the bore.

7. The apparatus according to claim 6, wherein the indicator comprises:
   (a) an indicator head, the indicator head having a guide aperture therethrough,
   (b) an indicator positioning rod extending from the indicator head, the rod in slidable engagement with the bore.

8. The apparatus according to claim 5, wherein the positioning block has a first wall and a second wall, the first wall having a shoe extending therefrom, the shoe in slidable engagement with the channel of the fixture.

9. The apparatus according to claim 8, wherein the shoe has flanges extending therefrom, the flanges in securable engagement with the channel.

10. The apparatus according to claim 9, wherein the first wall of the positioning block has a first threaded aperture, the first threaded aperture in threaded engagement with a first set screw.

11. The apparatus according to claim 10, wherein the side wall of the positioning block has a bore therethrough, the side wall having a side threaded aperture intersecting the bore, the side threaded aperture in threaded engagement with a second set screw.

12. The apparatus according to claim 3, wherein the fixture has a plurality of openings located adjacent the side edges of the first face.

13. The apparatus according to claim 12, wherein the template further has locator pins disposed along the second edge of the template, the locator pins being alignable with the openings in the first face of the fixture, the locator pins in removable engagement with the openings.

14. The apparatus according to claim 13, wherein the fixture has indentations at the corners of the first edge.

15. The apparatus according to claim 14, wherein the template further has a top edge and a bottom edge, the template having a locator pin disposed along the bottom edge adjacent the first edge, the locator pin in engagement with a selected one the indentations.

16. The apparatus according to claim 3, wherein the fixture has a plurality of grooves located adjacent the side edges of the first face.

17. The apparatus according to claim 16, wherein the template has projections disposed along the second edge of the template, the projections being alignable with the grooves in the first face of the fixture, and in removable engagement with the grooves.

18. The apparatus according to claim 17, wherein the fixture has indentations at the corners of the first edge.

19. The apparatus according to claim 18, wherein the template further has a top edge and a bottom edge, the template having a projection disposed along the bottom edge adjacent the first edge, the projection in removable engagement with a selected one of the indentations.

20. The apparatus according to claim 3, wherein the fixture has a plurality of channels formed along its length adjacent the side edges, the channels open to the first edge or the second edge of the fixture, the channels open to the second face of the fixture.

21. The apparatus according to claim 20, wherein the positioning block has a first wall and a second wall, the first wall having a shoe extending therefrom, the shoe in slidable engagement with the channels of the fixture.

22. The apparatus according to claim 2, wherein a centering guide is provided on the fixture.

23. An apparatus for transferring measurements from a diagnostic image to a body site, comprising:
   (a) a fixture for receiving a body part onto which a measurement is to be transferred, the fixture comprising:
      (1) a base having a first edge, a second edge, side edges, a first surface, and a second surface;

(2) an upstanding wall having a first edge, a second edge, opposite side edges, a first face, and a second face;

(b) a template removably attached to the fixture, the template having a first edge, a second edge, and opposite marking surfaces;

(c) a positioning block slideably mounted on the upstanding wall;

(d) an indicator in slidable engagement with the positioning block, whereby the indicator is moveable in orthogonal directions relative to the fixture and template.

24. The apparatus according to claim 23, wherein the upstanding wall has a channel formed along its length adjacent one of the side edges, the channel open to the first edge or the second edge of the fixture, the channel open to the second face of the fixture.

25. The apparatus according to claim 24, wherein the second face of the fixture has flanges constricting the channel opening in the second face of the fixture.

26. The apparatus according to claim 23, wherein the positioning block has a bore therethrough.

27. The apparatus according to claim 26, wherein the indicator is in slidable engagement with the bore.

28. The apparatus according to claim 27, wherein the indicator comprises:

(a) an indicator head, the indicator head having a guide aperture therethrough, (b) an indicator positioning rod extending from the indicator head, the rod in sliding engagement with the bore.

29. The apparatus according to claim 26, wherein the positioning block has a first wall and a second wall, the first wall having a shoe extending therefrom, the shoe in slidable engagement with the channel of the fixture.

30. The apparatus according to claim 29, wherein the shoe has flanges extending therefrom, the flanges in securable engagement with the channel.

31. The apparatus according to claim 30, wherein the first wall of the positioning block has a first threaded aperture, the first threaded aperture in threaded engagement with a first set screw.

32. The apparatus according to claim 31, wherein the side wall has a bore therethrough, the side wall having a side threaded aperture intersecting the bore, the side threaded aperture in threaded engagement with a second set screw.

33. The apparatus according to claim 23, wherein the fixture has a plurality of openings located adjacent the side edges of the first face.

34. The apparatus according to claim 33, wherein the template has locator pins disposed along the second edge of the template, the locator pins being alignable with the openings in the first face of the fixture, and in removable engagement with the openings.

35. The apparatus according to claim 34, wherein the fixture has indentations at the corners of the first edge.

36. The apparatus according to claim 35, wherein the template further has a top edge and a bottom edge, the template having a locator pin disposed along the bottom edge adjacent the first edge, the locator pin in engagement with a selected one of the indentations.

37. The apparatus according to claim 23, wherein the fixture has a plurality of grooves located adjacent the side edges of the first face.

38. The apparatus according to claim 37, wherein the template has further has projections disposed along the second edge of the template, the projections being alignable with the grooves in the first face of the fixture, and in removable engagement with the grooves.

39. The apparatus according to claim 38, wherein the fixture has indentations at the corners of the first edge.

40. The apparatus according to claim 39, wherein the template further has a top edge and a bottom edge, the template having a projection disposed along the bottom edge adjacent the first edge, the projection in engagement with a selected one of the indentations.

41. The apparatus according to claim 23, wherein the fixture has a plurality of channels formed along its length adjacent the side edges, the channels open to the first edge or the second edge of the fixture, the channels open to the second face of the fixture.

42. The apparatus according to claim 41, wherein the positioning block has a first wall and a second wall, the first wall having a shoe extending therefrom, the shoe in sliding engagement with the channels of the fixture.

43. The apparatus according to claim 23, wherein a centering guide is provided on the fixture.

44. An apparatus for use in transferring measurements from a diagnostic image to a body site, comprising:

(a) a fixture for receiving a body part onto which a measurement is to be transferred;

(b) a template removably attached to the fixture onto which a measurement may be transferred from a diagnostic image; and, (c) an indicator movable relative to the fixture and the template, the indicator being movable in orthogonal directions, the indicator alignable with a measurement transferred to the template, wherein the indicator has a guide aperture for guiding a marking device for marking a body part.

45. The apparatus according to claim 44, further comprising a positioning block, wherein the indicator is in sliding engagement with the positioning block, the positioning block for permitting movement of the indicator in orthogonal directions relative to the fixture and the template.

46. The apparatus according to claim 45, wherein the positioning block is in slidable engagement with the fixture.

47. The apparatus according to claim 46, wherein the positioning block has a bore therethrough.

48. The apparatus according to claim 47, wherein the indicator is in slidable engagement with the bore.

49. The apparatus according to claim 48, wherein the indicator comprises:

(a) an indicator head, the indicator head having the guide aperture therethrough, (b) an indicator positioning rod extending from the indicator head, the rod in slidable engagement with the bore.

* * * * *